US008667968B2

(12) United States Patent
Resnic

(10) Patent No.: US 8,667,968 B2
(45) Date of Patent: *Mar. 11, 2014

(54) CONDOM

(76) Inventor: Daniel Resnic, Culver City, CA (US)

( * ) Notice: Subject to any disclaimer, the term of this patent is extended or adjusted under 35 U.S.C. 154(b) by 141 days.

This patent is subject to a terminal disclaimer.

(21) Appl. No.: 12/943,287

(22) Filed: Nov. 10, 2010

(65) Prior Publication Data

US 2011/0303226 A1 Dec. 15, 2011

Related U.S. Application Data

(63) Continuation-in-part of application No. 12/814,647, filed on Jun. 14, 2010, now Pat. No. 8,136,528.

(51) Int. Cl.
*A61F 6/02* (2006.01)
*A61F 6/04* (2006.01)
*A41D 19/00* (2006.01)
*B05D 3/00* (2006.01)

(52) U.S. Cl.
USPC ........... 128/844; 128/842; 128/917; 128/918; 427/2.3; 600/38; 600/39; 600/41

(58) Field of Classification Search
USPC ......... 128/830, 834–837, 842, 844, 917, 918; 427/2.3; 206/69; 600/39–41
See application file for complete search history.

(56) References Cited

U.S. PATENT DOCUMENTS

| | | | | |
|---|---|---|---|---|
| 4,640,270 | A * | 2/1987 | Chin | 600/39 |
| 4,961,734 | A * | 10/1990 | Kassman | 604/349 |
| 5,515,862 | A * | 5/1996 | Artsi et al. | 128/830 |
| 5,549,196 | A * | 8/1996 | Kassman | 206/69 |
| 5,605,164 | A * | 2/1997 | Wilson, III | 128/842 |
| 5,701,915 | A * | 12/1997 | Wilson, III | 128/842 |
| 6,223,747 | B1 * | 5/2001 | Rudge et al. | 128/844 |
| 6,478,027 | B1 * | 11/2002 | Serrano et al. | 128/844 |
| 6,520,922 | B2 * | 2/2003 | Michelle | 600/562 |
| 8,025,062 | B2 * | 9/2011 | Osterberg | 128/844 |
| 8,136,528 | B2 * | 3/2012 | Resnic | 128/844 |
| 2004/0099274 | A1 * | 5/2004 | Osterberg | 128/844 |
| 2005/0061328 | A1 * | 3/2005 | Reddy et al. | 128/830 |
| 2006/0289012 | A1 * | 12/2006 | Reddy et al. | 128/844 |
| 2009/0199859 | A1 * | 8/2009 | Glenn | 128/844 |

FOREIGN PATENT DOCUMENTS

WO WO 2007/098428 8/2007

* cited by examiner

*Primary Examiner* — Patricia Bianco
*Assistant Examiner* — Brandon L Jackson
(74) *Attorney, Agent, or Firm* — Trojan Law Offices

(57) ABSTRACT

This invention relates to condoms, prophylactics and contraceptive devices made of silicone rubber having a body comprising a plurality of sections that are capable of folding telescopically, such that each section folds into an adjoining section.

11 Claims, 3 Drawing Sheets

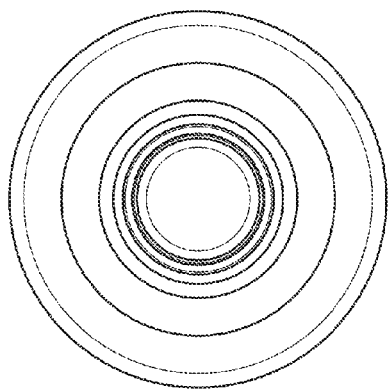
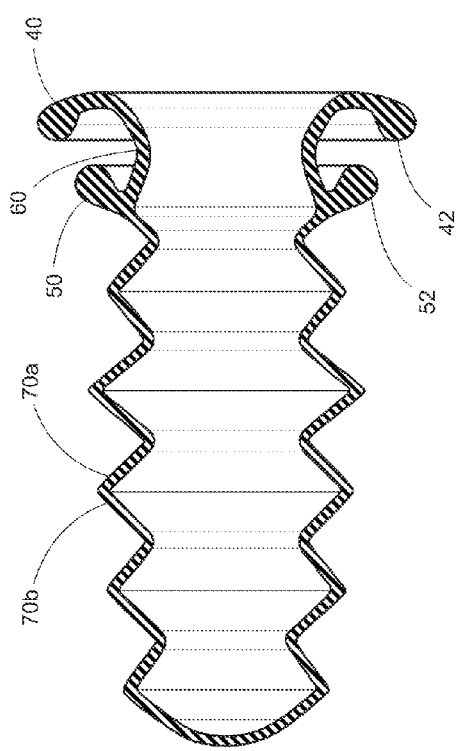
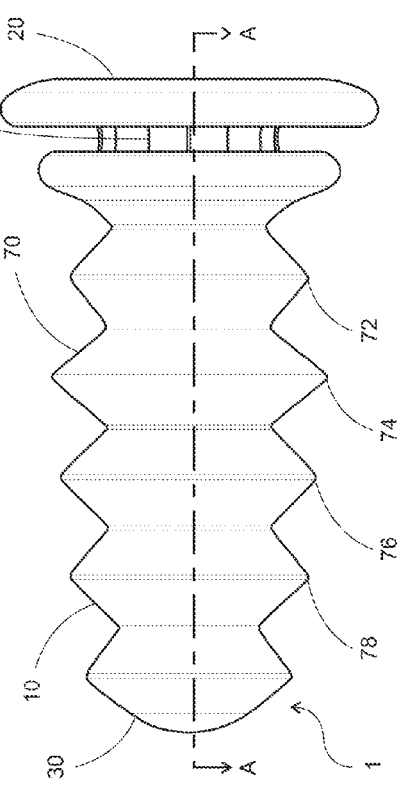

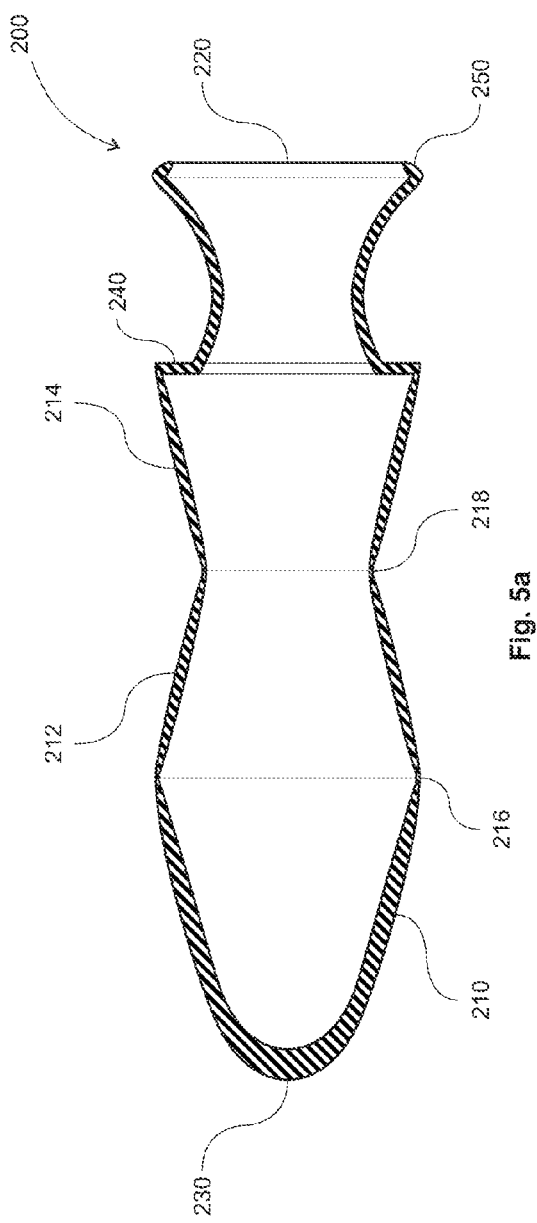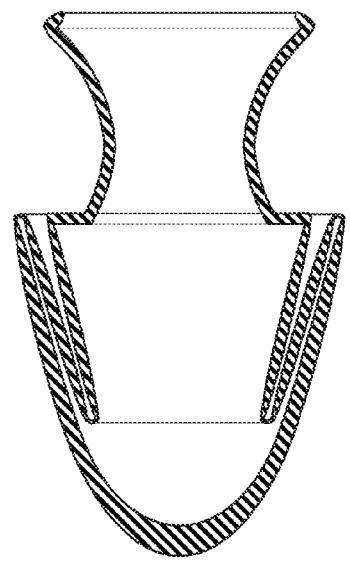

CONDOM

STATMENT OF PRIORITY

The present application is a continuation-in-part of U.S. patent application Ser. No. 12/814,647, filed on Jun. 14, 2010 now U.S. Pat. No. 8,136,528.

FIELD OF THE INVENTION

This invention relates to a condom for contraceptive and prophylactic use. In particular, this invention relates to an improved receptive condom for use in vaginal or anal intercourse, to prevent sexually transmitted diseases.

BACKGROUND OF THE INVENTION

The present invention is directed to overcoming problems associated with traditional thin membrane condoms in the fight against sexually transmitted diseases, including the spread of the human immunodeficiency virus (HIV) that can result in acquired immune deficiency syndrome (AIDS).

Protection from sexually transmitted diseases is a public health concern that affects all people, regardless of sexual orientation, nationality or age group. Since the onset of AIDS in the early 1980s, the AIDS pandemic has particularly affected the gay community, with gay men comprising approximately two-thirds of all AIDS cases in the United States. However, an increasing number of heterosexual women and men are becoming infected. In the fight against the spread of AIDS, the medical profession, as well as governmental and health organizations, have strongly advocated the use condoms to combat the transmission of HIV. Condoms conventionally come in male and female varieties.

A male condom is of the type worn on the penis by the active male partner during sexual intercourse. The traditional male condom has an elongated tubular sheath, typically made of a thin, soft material such as latex or polyurethane, or some type of fine animal skin. The condom is conventionally made quite thin in order to provide acceptable tactile stimulation for the active male user.

The tubular sheath of the male condom is open at one end for insertion of the penis, and closed at the other end to trap ejaculate of seminal fluids. The conventional condom is donned by unrolling, stretching and pulling the sheath onto the erect penis. In most varieties, the open end generally has a peripheral bead that functions as a constricted rim to prevent the condom from slipping.

Generally, the male condom is elastically fitted to the penis, and during coitus it remains outstretched and taut, which can increase the hazard of the condom being torn during use. The integrity of the condom can also be compromised by leakage and slippage. Hence, male condoms are well known to be only partially effective in the prevention of sexually transmitted diseases, such as HIV. Studies have shown that commercial thin-membrane latex male condoms can have a failure rate up to 17%.

Not only do traditional male condoms have an unacceptably high risk of failure, such condoms also suffer from a number of other shortcomings that can discourage their use, thus inhibiting their effectiveness in the fight against the spread of AIDS. One drawback is that the use of a condom can interrupt sexual intimacy because the condom has to be donned onto the erect penis after arousal. Another drawback is that after sexual intercourse is completed, the condom may slip off as the penis softens, which may cause unwanted leakage of semen and/or infectious matter.

Yet another disadvantage of the traditional male condom is the loss of sensation experienced by the active male caused by the fact that the condom must be tight-fitting in order to stay in place. The conventional condom does not permit adequate sensitivity for the active male during sexual intercourse because it constricts sensation. Also, because the condom is fitted to move along with the penis, it prevents direct tactile contact and friction between the penis of the active partner and the vaginal or rectal wall of the passive partner during sexual intercourse.

Not least, most traditional male condoms are typically constructed in a single, standard size, which does not accommodate penises of different sizes. Such construction can be uncomfortable for the male wearer when the standard size will not fit.

In addition to male condoms, there are also female condoms, which are barrier devices made to be worn internally by the female partner. The conventional female condom is typically comprised of a thin, pouch liner with a closed end and a large open end. The large open end is generally provided with a stiff ring, attached to hold the mouth of the liner open outside of the vagina. The closed end can also be provided with another ring to position the closed end against the cervix.

One of the disadvantages of a female (i.e. receptive) condom is that there is a risk that the condom can slip or become dislodged during sexual intercourse. For a female condom to be an effective barrier to pregnancy and/or the transmission of sexual diseases, it is essential that, even during repeated and rigorous contacts, the penis is unable to penetrate the vagina outside the condom. A number of condoms have attempted to address such problems.

An example of a female condom is disclosed in U.S. Pat. No. 4,945,923 to Evans et al. This patent discloses a contraceptive device to be worn by a female, having an outer ring adapted to be positioned exterior to the vaginal introitus of a wearer and an inner ring adapted to anchor the inner end of the device to the cervix of the wearer so that the device will not inadvertently fall out of the vaginal cavity.

Another example of a female condom is disclosed in U.S. Pat. No. 6,223,747 to Rudge et al., which discloses an embodiment having a large ring and, beyond it at the open end, a smaller ring having a diameter about half that of the large ring. According to Rudge et al., when the condom is inserted into the vagina the penis is passed through the small ring as well as the larger ring, which remains outside the vagina. When the penis is subsequently withdrawn, it is gripped lightly by the smaller ring so that the condom is simultaneously withdrawn form the vagina. Rudge et al. teaches that the ring remains outside the vaginal cavity. Rudge et al. further discloses that the female condom has grooves so that it folds in a bellows like manner in order to be collapsible to a substantially flat condition prior to use.

Like most common commercial condoms, the condom disclosed by Rudge et al. is formed of latex or polyurethane by a dip moulding process. Because it is made of thin latex, the condom is flaccid and thus susceptible to bunching during use. Specifically, the rounded grooves taught by Rudge et al. are formed with a thin flaccid membrane and do not have sufficient structural rigidity to collapse without bunching. Nor do the grooves facilitate the expansion or contraction of the condom. And the grooves do not function to improve traction between the condom and the cavity of the receptive partner.

U.S. Pat. No. 7,047,975 to Austin et al. discloses a female condom having an outer ring and an inner ring. The outer ring is sized such that it is disposed externally, generally contacting the region surrounding the vaginal opening (the vulva), and the perineum of the female user. The inner ring is configured and disposed in relation to the outer ring such that when the female condom is inserted into the vaginal canal and is fully deployed, the inner ring locates itself and presses against the vaginal wall surfaces at a distal side of the introitus.

Last, there is known a hybrid male and female condom. U.S. Pat. No. 4,798,600 to Meadows discloses a condom having a first ring at the opening of the condom and a second ring midway along the length of the condom sheath, such that the second ring effectively divides the condom into a male portion and a female portion. Meadows discloses that the first ring functions to hold the condom snugly around the penis to prevent the penis from sliding out of the condom. The second ring maintains the condom in a centered position during intercourse so that the male portion and female portion are each properly positioned. In Meadows, the second ring does not have sufficient structure to be inserted into the vaginal cavity; rather, it sits on the outside of the vaginal opening.

SUMMARY OF THE INVENTION

In view of the foregoing, it is an object of the present invention to provide a condom that is safer than available commercial condoms.

It is an object of the present invention to provide an improved condom for use in receptive intercourse.

It is an object of the present invention to provide an improved condom that can be easily inserted for receptive intercourse.

It is an object of the present invention to provide an improved condom that can be applied before intercourse so as not to interrupt sexual activity.

It is an object of the present invention to provide an improved condom that does not slip during intercourse.

It is an object of the present invention to provide an improved condom that can loosely accommodate a penis so as not to cause loss of sensation.

It is an object of the present invention to provide an improved condom that can enhance direct tactile contact and friction between the penis of the internal condom wall during sexual intercourse.

It is an object of the present invention to provide an improved condom that can readily stretch beyond one size to accommodate penises of different sizes, from smaller to extra large.

In accordance with the objects of the present invention, a condom according to an embodiment of the invention has a sheath body with an open end and a closed end, two collars proximate to the open end, and a series of accordion pleats on the sheath body. Unlike most common condoms that have a single ring at the open end, the condom according to this embodiment has two flanged collars. The first collar is an external flange at the open end of the condom body, which functions to engage the outside of an orifice when the condom is inserted into a body cavity. The second collar is an internal flange located on the neck of the condom in proximity, or adjacent, to the first collar. When the condom is inserted into a body cavity, the second collar is engaged on the inside of the orifice to prevent the condom from slipping out of the body cavity.

The sheath body of the condom has a series of circular accordion pleats. The pleats enable the condom to contract or expand along the longitudinal axis of the condom as necessary to fit the body cavity and to accommodate the penis. In order for the pleats to expand and contract as desired, the condom is made of heavy gauge silicone, with a thickness of at least 0.06 inches, so that the condom has a structural rigidity that enables each pleat to contract or expand independently of the other pleats. This contributes to the mechanical "pop" action that facilitates the automatic expansion and contraction of the condom. And in this way, each pleat segment can expand or contract without causing the entire condom to become too springy. The pleats also minimize bunching, thereby facilitating insertion of the condom into the body cavity. Further, the folds of the pleats improve traction between the condom and the cavity, and the accordion contraction and expansion of the condom can enhance sensation during sexual activity.

In a preferred embodiment of the invention, the pleats are of varying diameters. The smaller pleats can stack in a bowl shape inside the larger pleats, which allows the condom to be compressed substantially flat to facilitate packaging.

In order to make a condom according to the objectives of the present invention, the condom is preferably made from heavy gauge silicone so that the condom is sufficiently thick to have sufficient structural rigidity and tensile strength to function as described. Conventional condoms, commonly made from latex or other thin materials, do not provide the requisite structural rigidity and tensile strength to enable the pleated construction described herein.

To make a thick condom having the features of the present invention, it is necessary to employ a method of injection molding using heavy gauge silicone. A 2-part silicone polymer is forced into a mold cavity where it is heated and then hardens to the configuration of the condom having the features of the present invention, allowing the condom to be molded with pleats, collars, and ribs as described. By contrast, conventional thin condoms are made by a dipping process. The basic consideration in fabricating conventional condoms is to make the condoms as thin as possible to maximize the transfer of sensation through the material. Since the goal is to optimize thinness (not thickness), the most popular commercial condoms are made of latex. Typically, latex condoms are made feeding a latex compound into temperature-controlled tanks into which glass formers are dipped. The formers pick up a thin film of latex. The latex coating is then dried and, after drying, the condoms are then passed through an oven to vulcanize the latex. This dipping process is ineffective for making thick condoms with the pleats as described.

The present condom provides a more comfortable fit for the active partner as it loosely accommodates the penis so that movement of the penis is possible during coitus. The condom also provides increased stimulation for the passive partner because the accordion pleats rub against the vaginal or rectal wall during intercourse.

An important aspect of the present condom is that it can be used either as a male or female condom. The condom can be donned on a penis as a male condom by inserting the penis until the accordion pleats extend to the desired length. Unlike the familiar rolled condom that must be unrolled down the shaft of the penis, and which can be difficult for the consumer to orient correctly, the present condom can be easily donned without unrolling by manually extending it to insert the penis, or the penis can be inserted directly into the collapsed condom. The condom will automatically expand in response to the insertion of the penis.

The present condom can also function as a receptive condom by inserting it into the vaginal or anal cavity prior to sexual activity. It is contemplated that the novel characteristics of the condom make it uniquely suited as a prophylactic device for receptive vaginal or anal intercourse. As a receptive condom it may be applied prior to intercourse without requiring the participation or acquiescence of the active partner.

Since the receptive condom may be inserted before intercourse, it does not necessarily interrupt or interfere with the sexual intercourse.

The condom suffers from none of the limitations inherent in latex condoms. Under laboratory testing, latex condoms have proven to have deficient strength (e.g. tensile and tear properties) and durability, and are also allergic. Most importantly, it is widely known in the art and independent testing has shown that latex condoms do not provide 100% protection against sexually communicable diseases, such as HIV. Because the condom of the present invention is made of silicone rubber, it has demonstrated superior strength and durability, providing 100% protection against the transmission of sexually transmitted diseases as well as protection against unintentional pregnancies.

While the foregoing describes the present invention in relation to the drawings and embodiments, it is to be understood that the description is not intended to limit the scope of the invention to the drawings or embodiments described herein. To the contrary, the description is intended to cover all alternative modifications and equivalents that may be included in the spirit and the scope of the invention as defined by the appended claims.

In another preferred embodiment of the invention, the condom has a plurality of sections that are capable of telescopically collapsing, such that the sections overlap inside one another, with each section folding into an adjoining section until contained in the last section, with the closed end cupping the collapsed sections. By overlapping the sections telescopically, the body of the condom is made more structurally rigid so that the condom can be more easily inserted by the use of one or two fingers, eliminating the need to employ a special insertion device as commonly required with some conventional female condoms. Further, because the condom is telescopically collapsed, it does not bunch or bulk up upon insertion, thus avoiding a common problem with condoms that are designed to fold or stack sequentially.

The condom is inserted with the sections remaining folded until penetration of the penis acts to fully extend the sheath body. It is the insertion of the penis into the condom that causes the sections to extend. This not only reduces the overall length of the condom so that it can be more compactly packaged, its compactness also enables the condom to be comfortably inserted and accommodated inside the body orifice until commencement of sexual activity.

Because the condom is fabricated of heavy gauge silicone by injection molding, the different parts or sections of the condom can be made to have varying material properties. For example, the telescopically collapsible sections can be of varying thicknesses such that they consistently bend at the thinnest points, which define the joints connecting the sections.

DESCRIPTION OF THE DRAWINGS

FIG. 1 is a side view of an embodiment of the invention.

FIG. 2 is a section view of the embodiment shown in FIG. 1.

FIG. 3 is a front view of the embodiment shown in FIG. 3.

FIG. 5a is a sectional side view of another embodiment of the condom.

FIG. 5b is a sectional side view of the embodiment of the condom telescopically folded.

DETAILED DESCRIPTION OF THE INVENTION

Figure 4A:
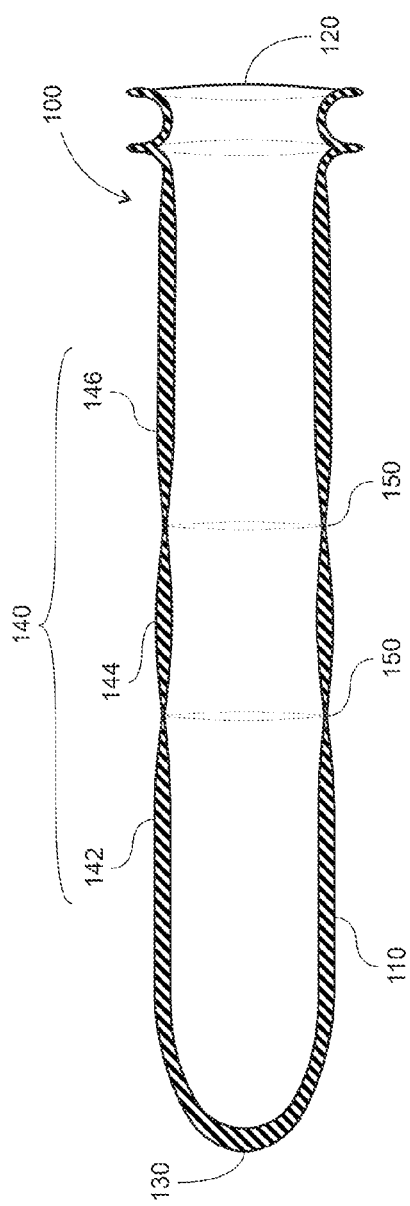
FIG. 4a is a sectional side view of an embodiment of the condom having tapered walls.
Figure 4C:
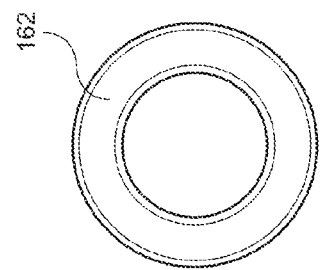
FIG. 4c is an end view of the embodiment of the condom shown in FIG. 4b.

As shown in FIGS. 1, 2 and 3, the condom 1 of the present invention has a sheath body 10 with a proximal end 20 that is open and a distal end 30 that is closed. In a preferred embodiment, the open end 20 has a diameter of approximately 1.0 inch, although the opening can expand to at least three times that diameter due to the condom 1 being made of stretchable material, such as heavy gauge silicone rubber.

At the open end 20, the condom 1 has a first collar 40. In a preferred embodiment, the first collar 40 is defined by an annular flanged rim 42 that is turned towards the sheath body 10 as shown in FIG. 2, and preferably having a diameter of at least 2.5 inches.

Adjacent to first collar 40 is a second collar 50, somewhat smaller than first collar 40, the second collar 50 having a diameter of approximately 2.0 inches. The second collar 50 is similarly defined by an annular flanged rim 52 that is turned towards the first collar 40 as shown in FIG. 2, forming a neck portion 60 between first collar 40 and second collar 50. In an embodiment of the invention, the neck portion 60 has a plurality of ribs 62 arranged in parallel to the longitudinal axis about the circumference of neck portion 60. The plurality of ribs 62 function to strengthen the neck portion 60 so as to minimize twisting during sexual activity.

Condom 1 has a plurality of accordion pleats 70 on the sheath body 10. Each of the pleats 70 form a V-shaped fold, defined by a first surface 70a that extends away from the longitudinal axis A of the body 10 and a second surface 70b that slopes toward the longitudinal axis A, such that a crease is formed at each intersection of the surfaces 70a and 70b. In a preferred embodiment as shown in FIGS. 1 and 2, there are four pleats 72, 74, 76, 78 that form the sheath body between the second collar 50 and the closed end 30. Each pleat 72, 74, 76, 78 is formed in a V-shaped configuration, such that they define a series of adjoining peaks and valleys. The peaks and valleys of the pleats 70 are of varying dimensions. As shown in FIGS. 1 and 2, which shows the condom 1 in a normally expanded state prior to use but not the fully distended state of use, the outer diameters (defined as peak to peak in the cross-section) range from approximately 1.5 inches to 1.8, and the inner diameter (defined as trough to trough in the cross-section) range from approximately 0.8 inches to 1.0 inches, though these dimensions can vary greatly because the condom 1 is stretchable and expandable.

In order for the pleats 70 to expand and contract as necessary to fit the body cavity and accommodate the penis, the condom 1 must be made to have sufficient structural rigidity and tensile strength. Latex and other traditional thin materials from which conventional condoms are commonly made do not provide the requisite structural rigidity and tensile strength to enable the pleated construction described herein. The condom of the present invention is made of heavy gauge silicone. In a preferred embodiment of the invention, the heavy gauge silicone is at least 0.06 inches thick, so that the pleats 72, 74, 76 and 78 have sufficient structural rigidity to enable each one to independently contract or expand. The heavy gauge silicone must be sufficiently thick for the pleats 70 to be substantially creased along the folds because the creasing permits each pleat to expand or contract by itself, one at a time, so that the overall expansion and compression of the condom 1 is not too springy. This contributes to the mechanical "pop" action that facilitates the automatic expansion and contraction of the condom. The creasing of the pleats also prevents the condom from collapsing laterally, thus enabling the penis to slide freely in the condom 1. The creasing not only helps to prevent or minimize bunching, the folds of the pleats 70 improve traction between the condom and the cavity. The creasing and the movements of the pleats also enhance sensation during sexual activity.

To use condom 1 for vaginal intercourse, for example, the closed end 30 is inserted into the vagina, with the first collar 40 at the open end 20 functioning to engage the outside of the vaginal opening. The second collar 50 functions to engage the inside of the vaginal opening to prevent the condom from slipping out of the body cavity.

Figure 4B:
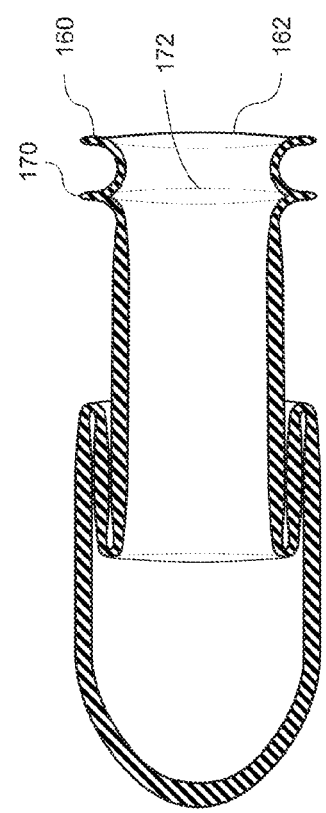
FIG. 4b is a sectional side view of the embodiment of the condom telescopically folded.

In another embodiment of the invention as shown in FIGS. 4a and 4b, the condom 100 of the present invention has a sheath body 110 with an open end 120 and a closed end 130. Because condom 100 is made of heavy gauge silicone using a fabrication method of injection molding, the different parts or sections of the condom 100 can be made to have different material properties. In the preferred embodiment of the invention, for example, the closed end 130 can be injected with a silicone that has a higher material strength than in the sheath body 110. In particular, the silicone in the closed end 130 can have a higher durometer (i.e. hardness) than in the sheath body 110. Alternatively, the closed end 130 can be comprised of a silicone having a greater thickness than in the sheath body 110. By reinforcing the closed end 130 with a harder or thicker material, the condom 100 is strengthened at the point of insertion.

The sheath body 110 has a plurality of sections 140. In the preferred embodiment as shown in FIG. 4a, sheath body 110 has sections 142, 144, and 146 adjoined in series. Section 142 is proximate to closed end 130. Section 142 adjoins section 144 at a first joint 150. Section 144 adjoins section 146 at a second joint 150. Section 146 is proximate to open end 120. The sections 140 are capable of telescopically folding, such that section 146 folds inside section 144, which in turn folds inside section 142 as shown in FIG. 4b. In this way, the plurality of sections 140 can be telescopically converged, with sections 142, 144, and 146 overlapping one inside the other.

The telescoped layers increase the structural rigidity of the sheath body 100 where the sections 142, 144, and 146 overlap. This enables the condom 100 to be more easily inserted by the use of one or two fingers, eliminating the need to employ a special insertion device as commonly required with some conventional female condoms. Further, because the sections 140 are telescopically collapsed, when the condom 100 is inserted into a body orifice the sheath body 110 does not bunch or bulk up at the point of insertion. As such, the telescopic folding of the sections 140 avoids bunching that is a common problem with conventional female condoms.

The condom 100 is inserted with the sections 140 remaining telescopically collapsed until penetration of the penis acts to fully extend the sheath body 110. It is the insertion of the penis into the condom 100 that causes the sections 140 to extend. This enables the condom 100 to be comfortably and compactly accommodated inside the body orifice until commencement of sexual activity. When the penis is inserted into condom 100, lubrication on the outside of condom 100, which lubricates the overlapping sections 140, facilitates the smooth unfolding of the sections 140.

Again, because condom 100 is made of silicone by injection molding, the sheath body 110 can be made to have varying thicknesses. For example, each section 142, 144, and 146 can be tapered such that it becomes gradually thinner approaching the joints 150. Because the sections 140 are tapered at the joints 150, the sections 140 can more easily bend at the joints 150, defined by the difference in thickness or durometer, thus facilitating the collapsing and unfurling of sheath body 110. To further facilitate the telescopic collapsing and unfurling of sections 140, section 146 can be made to have a smaller diameter than section 144, such that section 146 more easily folds within section 144. In turn, section 144 can be made to have a smaller diameter than section 142, such that section 144 more easily folds within section 142.

At the open end 120, the condom 100 has an external collar 160. In the preferred embodiment, the external collar 160 is defined by a flat annular flange 162 that functions to engage the external side of the vaginal or anal opening to prevent the condom 100 from forcing into the body orifice during sex.

An internal collar 170 is located on sheath body 110 approximate to external collar 160. The internal collar 170 is somewhat smaller than the external collar 160, and it is similarly defined by a flat annular flange 172. The internal collar 170 is covered by sheath body 110 such that it projects inside sheath body 110. The internal collar 170 functions to engage an internal side of the vaginal or anal opening to prevent condom 100 from forcing out the body orifice during sex.

In another embodiment of the invention as shown in FIG. 5a, condom 200 has a sheath body 210 with an open end 220 and a closed end 230. The sheath body 210 is further comprised of a first intermediate section 212 and a second intermediate section 214.

First intermediate section 212 is proximate to closed end 230. First intermediate section 212 adjoins closed end 230 at a first circumferential joint 216. First intermediate section 212 adjoins second intermediate section 214 at a second circumferential joint 218. Second intermediate section 241 is proximate to internal collar 240. First circumferential joint 216 has a larger diameter than second circumferential joint 218. For example, in a preferred embodiment of the invention, first circumferential joint 216 has a diameter of 2.25 inches, and second circumferential joint 218 has a diameter of 1.38 inches. Second circumferential joint 218 has a smaller diameter than internal collar 240. For example, in the preferred embodiment of the invention, second circumferential joint 218 has a diameter of 1.38 inches, and internal collar 240 has an outer diameter of 2.00 inches.

First intermediate section 212 is capable of telescopically folding inside closed end 230 at first circumferential joint 216. Second intermediate section 214 is capable of telescopically folding inside first intermediate section 212 at second circumferential joint 218. In this way, the sheath body 210 is capable of telescopically collapsing, with second intermediate section 214 overlapping with first intermediate section 212 and closed end 230 such that the sections are folded one inside the other.

In an embodiment of the invention, the condom 200 further comprises an internal collar 240, which adjoins the second intermediate section 214. The internal collar 240 has a flat annular shape, defined by an outer circumferential edge 240a, which is contiguous with second intermediate section 214, and a smaller inner circumferential edge 240b, which characterizes the opening for penetration of the penis. The internal collar 240 functions to engage an internal side of a body orifice during sex to prevent the condom 200 from slipping out of said body orifice.

I claim:

1. A condom made of silicone rubber comprising:
   a body with an open end and a closed cup end, said body having a plurality of sections that are successively smaller towards said open end, said plurality of sections capable of telescopically folding such that said each section is contained in an adjoining section, wherein all said plurality of sections are sequentially contained in said cup end without bunching when said condom is collapsed, whereby said condom is telescopically collapsed when inserted into a body cavity; and wherein at least one of said section has two endpoints where it adjoins two other said sections said at least one section being tapered such that it is thickest at a midpoint between said two endpoints and thinnest at said endpoints.

2. The condom of claim 1 further comprising:
a first collar, said first collar having a first circumferential edge and a second circumferential edge with a flat annular section therebetween;
wherein said first collar engages an external side of a body orifice during sex to prevent said condom from slipping into said body orifice.

3. The condom of claim 2 further comprising:
a second collar, said second collar having a first circumferential edge and a second circumferential edge with a flat annular section therebetween;
said second collar capable of fitting in said cup end;
wherein said second collar engages an internal side of a body orifice during sex to prevent said condom from slipping out of said body orifice.

4. The condom of claim 3 wherein said second collar's first circumferential edge has a diameter smaller than that of said first collar's first circumferential edge.

5. The condom of claim 1 wherein said closed cup end is reinforced such that said closed end has a higher material strength than said body of said condom.

6. The condom of claim 5 wherein said closed cup end is comprised of silicone rubber having a higher durometer than in said body of said condom.

7. The condom of claim 5 wherein said closed cup end is comprised of silicone rubber having a greater thickness than in said body of said condom.

8. The condom of claim 1 further comprising:
a first section adjacent to said closed cup end;
a second section adjoining said first section, said second section capable of folding inside said first section; and
a third section adjoining said second section, said third section capable of folding inside said second section;

wherein said condom is made of silicone rubber such as to enable each said section to have sufficient structural rigidity to telescopically contract and extend.

9. The condom of claim 1 wherein at least one of said section has an endpoint where it adjoins another said section, said at least one section being tapered such that it becomes gradually thinner approaching said endpoint.

10. A condom comprising:
a body with a closed cup end;
a first intermediate section adjacent to said closed cup end, said first intermediate section adjoining said closed cup end at a first circumferential joint;
a second intermediate section smaller than said first intermediate section, said second intermediate section adjoining said first intermediate section at a second circumferential joint;
a flange collar forming an open end adjacent to said second intermediate section; and
an internal collar adjoining said second intermediate section, said internal collar engaging an internal side of a body orifice during sex to prevent said condom from slipping out of said body orifice;
wherein said condom is capable of telescopically collapsing said closed cup end against said flange collar by folding said first intermediate section inside said closed cup end and said second intermediate section inside said first intermediate section such that all said sections are sequentially contained within said cup end without bunching when said condom is collapsed, whereby said condom is telescopically collapsed when inserted into a body cavity.

11. The condom of claim 10 wherein said internal collar further comprises:
an outer circumferential edge, said outer circumferential edge contiguous with said second intermediate section;
an inner circumferential edge, said inner circumferential edge being smaller in diameter than said outer circumferential edge, said inner circumferential edge defining an opening therein.

* * * * *